(12) United States Patent
Myers et al.

(10) Patent No.: US 7,715,009 B1
(45) Date of Patent: May 11, 2010

(54) OPTICAL INSTRUMENT

(75) Inventors: Richard Myers, Gibsonia, PA (US); Edward A. Smierciak, Pittsburgh, PA (US); Joseph F. Lebarty, Pittsburgh, PA (US); George Gaffron, North Huntington, PA (US)

(73) Assignee: Teledyne Technologies Incorporated, Thousand Oaks, CA (US)

( * ) Notice: Subject to any disclaimer, the term of this patent is extended or adjusted under 35 U.S.C. 154(b) by 457 days.

(21) Appl. No.: 11/735,643

(22) Filed: Apr. 16, 2007

(51) Int. Cl.
*G01N 21/00* (2006.01)

(52) U.S. Cl. .................. 356/436; 356/437

(58) Field of Classification Search .......... None
See application file for complete search history.

(56) References Cited

U.S. PATENT DOCUMENTS

| | | | |
|---|---|---|---|
| 2,287,785 A | 6/1942 | Dean | |
| 5,617,212 A | 4/1997 | Stuart | |
| 5,751,423 A | 5/1998 | Traina et al. | |
| 5,831,730 A | 11/1998 | Traina et al. | |
| 5,999,257 A | 12/1999 | Myers et al. | |
| 6,781,695 B2 | 8/2004 | Hovan et al. | |

OTHER PUBLICATIONS

"Ultra-low level Dust Emissions Compliance Monitor, Model 4500 Premier," LAND Combustion and Environmental Monitoring, printed from http://www.landinst.com/combustion/products/dust_emissions_monitoring/4500P_dust_monitor.htm. on Apr. 23, 2007.

"Dust Emissions Compliance Monitor, Model 4500 MkII+," LAND Combustion and Environmental Monitoring, printed from http://www.landinst.com/combustion/products/dust_emissions_monitoring/4500mk2_dust_monitor.htm on Apr. 23, 2007.

"Dust Measurement", Sick Maihak, Inc., printed from http://www.sick.com/sickmaihak/product/categories/dustmonitors/en.html on Apr. 23, 2007.

FW100 Datasheet, Sick/Maihak, Inc., printed from www.sickmaihak.de/sickmaihak_de/products/categories/dustmonitors/fw100/en.html on May 30, 2007.

FW100 Product Information, Sick/Maihak, Inc., printed from www.sickmaihak.de/sickmaihak_de/products/categories/dustmonitors/fw100/en.toolboxpar.0002.file.tmp/PI_FW100_en_D08-00_8008903.pdf on May 30, 2007.

FWE200 Datasheet, Sick/Maihak, Inc., printed from www.sickmaihak.de/sickmaihak_de/products/categories/dustmonitors/fwe200/en.html on May 30, 2007.

(Continued)

*Primary Examiner*—Gregory J Toatley, Jr.
*Assistant Examiner*—Amanda H Merlino
(74) *Attorney, Agent, or Firm*—K&L Gates LLP

(57) ABSTRACT

An apparatus for measuring an optical property of a fluid. The apparatus may comprise a light source for projecting a beam of optical energy through the fluid and a reflector positioned opposite the fluid from the light source. The apparatus may also comprise receiver optics defining a receiver aperture. The reflector may be selected to under-fill the receiver aperture by a factor of at least 2.5. According to various embodiments, the apparatus may also comprise a reflector purge nozzle positioned at least partially between the reflector and the fluid. In addition to, or instead of the under-fill factor described above, the reflector may be selected to have a diameter less than a diameter of the reflector purge nozzle by a factor of at least 6.

14 Claims, 14 Drawing Sheets

OTHER PUBLICATIONS

"Model 440 Compliance Opacity Monitoring System", Thermo Fisher Scientific, printed from http://www.thermo.com/com/cda/product/detail/1,,14369,00.html on Apr. 23, 2007.

"D-R 290 Technical Specifications", Durag, Inc., printed from http://www.durag.com/html/ems/emsprod.html on Apr. 23, 2007.

Particle Size Measurement Instruments Technical Specifications (PPC), Process Metrix LLC, printed from http://www.processmetrix.com/ppc_tech_specs.htm on Aug. 22, 2007.

Norfleet, Stephen K., "Demonstrating Compliance with Low-Level Opacity Limits," Presented at EPRI CEMS Users Group Meeting, Columbus, Ohio, (May 3-5, 2006).

Meyers, et al., "Analysis of Conventional Dust Density Measurement Techniques With Indications of an Improved Approach Via Forward-Scattering Angular Analysis", presented to Air and Waste Management Association Annual Conference, (Jun. 1998).

Meyers, et al., "Application and Technological Issues Associated with Continuous Monitoring of Source Particulates"; presented to Electric Utilities Environmental Conference, Tucson, AZ, (Jan. 2004).

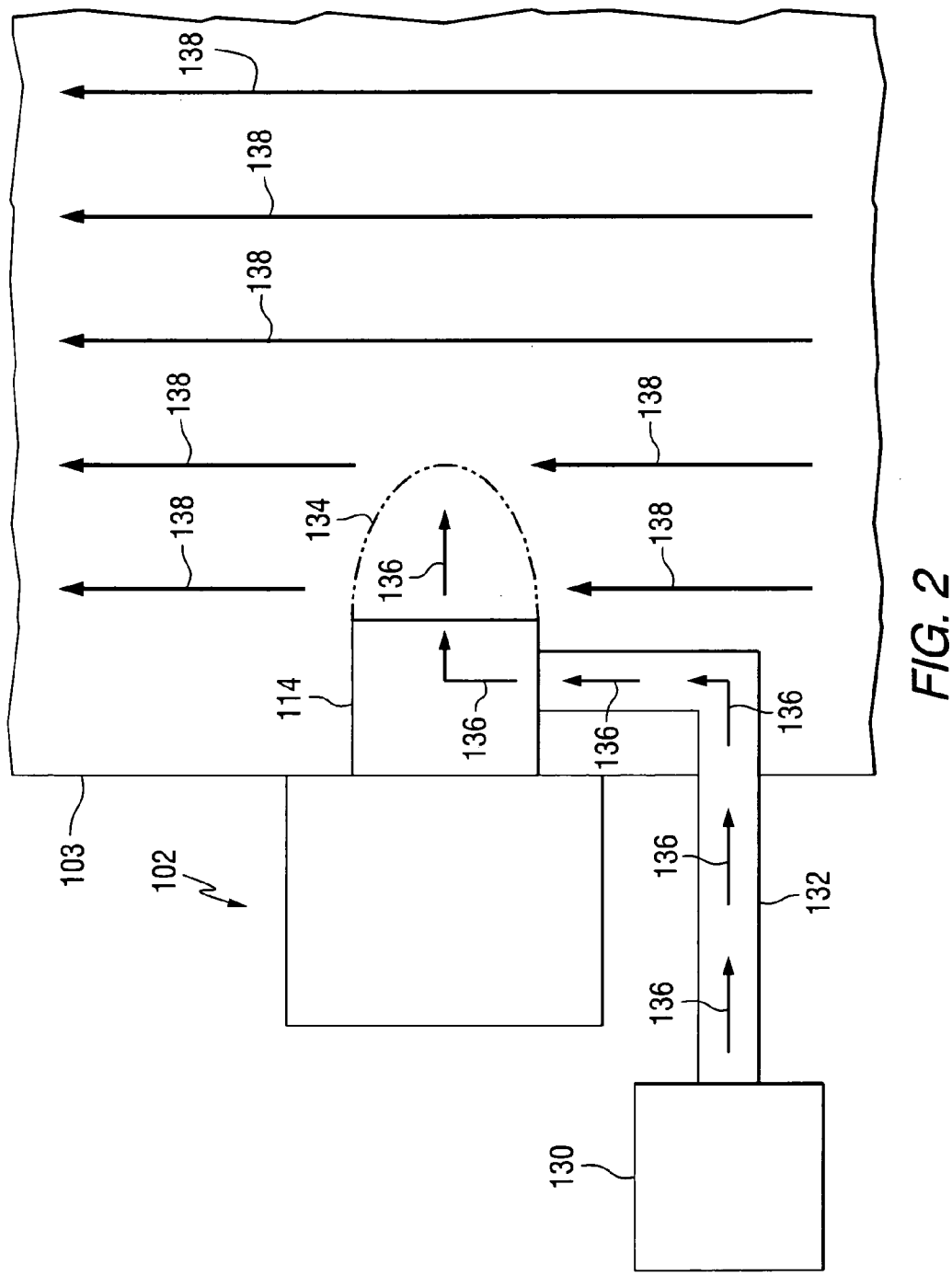

OPTICAL INSTRUMENT

BACKGROUND

Regulations in the United States and other nations place limits on the levels of pollution that can be emitted into the air or water by various processes. For example, the regulations limit the opacity, particulate matter content, and other properties of stack gas emitted by electric utilities, industrial and other sources. Many of these regulations require that outgoing stack gas be monitored to ensure compliance with the standards. Accordingly, instruments have been developed to monitor outgoing stack gas and other fluids.

Various existing instruments operate by directing a beam of optical energy across a stack or other fluid containing area and measuring the portion of the beam that is extinguished, scattered, or otherwise interacts with the fluid. One such device is a double-pass opacity monitor. A double-pass opacity monitor, such as opacity monitor 100 shown in FIG. 1, includes a transceiver assembly 102 on a first side of a fluid 101 and a reflector assembly 104 on a second side of the fluid 101 opposite the transceiver 102. The fluid 101 may be contained within a stack (not shown) positioned between the transceiver assembly 102 and reflector assembly 104. In use, a light source 108 of the transceiver assembly 102 emits a forward beam 120 of optical energy that is reflected by beam splitter 110 toward an aperture 106. An imaging lens 105 is present at or near the aperture 106 and directs the forward beam 120 out of a purge nozzle 114 of the transceiver assembly 102 and toward the reflector assembly 104. At the reflector assembly 104, the beam 120 is received by a purge nozzle 116 where it may be incident on corner cube reflector 112. The reflector 112 reflects a portion of the forward beam 120 back toward the transceiver assembly 102 as a reverse beam 122. The reverse beam 122 is incident on the aperture 106 and imaging lens 105, which focus the reverse beam 122 through the beam splitter 110 and onto a sensor 109. The difference between the intensity of the return beam 122 in a clear environment and the intensity of the return beam 122 when a fluid, such as stack gas 101, is present yields an indication of the opacity of the fluid 101.

FIG. 1 shows a typical prior-art configuration of the opacity monitor 100. As shown, the transceiver assembly 102 directs a diverging forward beam 120 across the stack, represented by the distance d, and toward the reflector assembly 104, where the beam 120 over-fills the reflector 112. That is, when the forward beam 120 is incident on the reflector 112, it has diverged to a diameter greater than that of the reflector 112. This wastes a portion of the optical energy of the beam 120, but greatly simplifies the process of aligning the transceiver assembly 102 and reflector assembly 104. The return beam 122 then traverses the distance d again, until it is incident on the aperture 106 and lens 105. The diameter of the reflector 112 is selected to configure the return beam 122 to approximately fill the aperture 106. It is not desirable to significantly over-fill the aperture 106 because this wastes additional optical energy. Also, in prior designs, it was thought undesirable to significantly under-fill the aperture 106 because this will reduce the intensity of the return beam, and consequently the signal-to-noise ratio of the monitor 100.

Although the opacity monitor 100 shown by FIG. 1 should theoretically produce accurate results, in practice, it does not. Opacity monitors, such as monitor 100, and other similar optical instruments, have long exhibited an unexplained negative bias when installed on a stack. That is, the instruments often produce an opacity reading that is lower than the actual opacity of the fluid 101. It is believed that this negative bias affects results at all observed opacity levels, however, it is most apparent in relatively clean stacks with relatively low opacity. In some of these stacks, the actual opacity of the stack gas is less than the amount of the negative bias, causing the instrument to read a negative opacity. Predictably, sources that report negative opacity have been subjected to scrutiny and accused of having malfunctioning monitors. Also, environmental regulatory agencies are believed to have penalized sources that report excessive negative opacity readings. Paradoxically, as sources have improved process control and installed more effective pollution control devices, their stacks have become cleaner and therefore more likely to exhibit a negative opacity reading as a result of the negative bias. There has been much speculation about the source of the negative bias, but there are still no satisfactory ways of dealing with it.

SUMMARY

In one general aspect, the present invention is directed to an apparatus for measuring an optical property of a fluid. The apparatus may comprise a light source for projecting a beam of optical energy through the fluid and a reflector positioned opposite the fluid from the light source. The apparatus may also comprise receiver optics defining a receiver aperture. The reflector may be selected to under-fill the receiver aperture by a factor of at least 2.5. According to various embodiments, the apparatus may also comprise a reflector purge nozzle positioned at least partially between the reflector and the fluid. In addition to, or instead of the under-fill factor described above, the reflector may be selected to have a diameter less than a diameter of the reflector purge nozzle by a factor of at least 6.

In another general aspect, the present invention is directed to another apparatus for measuring an optical property of a fluid. The apparatus may comprise a light source for projecting a light beam through the fluid and a reflector positioned opposite the fluid from the light source. The apparatus may also comprise receiver optics positioned opposite the fluid from the reflector. A purge nozzle may be positioned at least partially between the reflector and the fluid. Also, a purge flow generator may be configured to emit a stream of purge fluid out of the purge nozzle toward the fluid. The apparatus may additionally comprise a heater positioned to heat the stream of purge fluid, and a cool fluid duct for directing unheated fluid to the reflector.

In yet another general aspect, the present invention is directed to another apparatus for measuring an optical property of a fluid. This apparatus may comprise a light source for projecting a light beam through the fluid; a reflector positioned opposite the fluid from the light source; and receiver optics positioned opposite the fluid from the reflector. The apparatus may also comprise a purge nozzle positioned at least partially between the reflector and the fluid; and a purge flow generator configured to emit a stream of purge fluid through a first opening of the purge nozzle toward the fluid. According to various embodiments, the purge nozzle may define at least one mixing opening allowing the fluid to mix with the stream of purge fluid before the stream of purge fluid reaches the first opening.

DRAWINGS

Embodiments of the present invention are described herein, by way of example, conjunction with the following figures, wherein:

FIGS. 2, 2A and 2B show illustrations of an air lens, according to various embodiments;

DESCRIPTION

Figure 1:
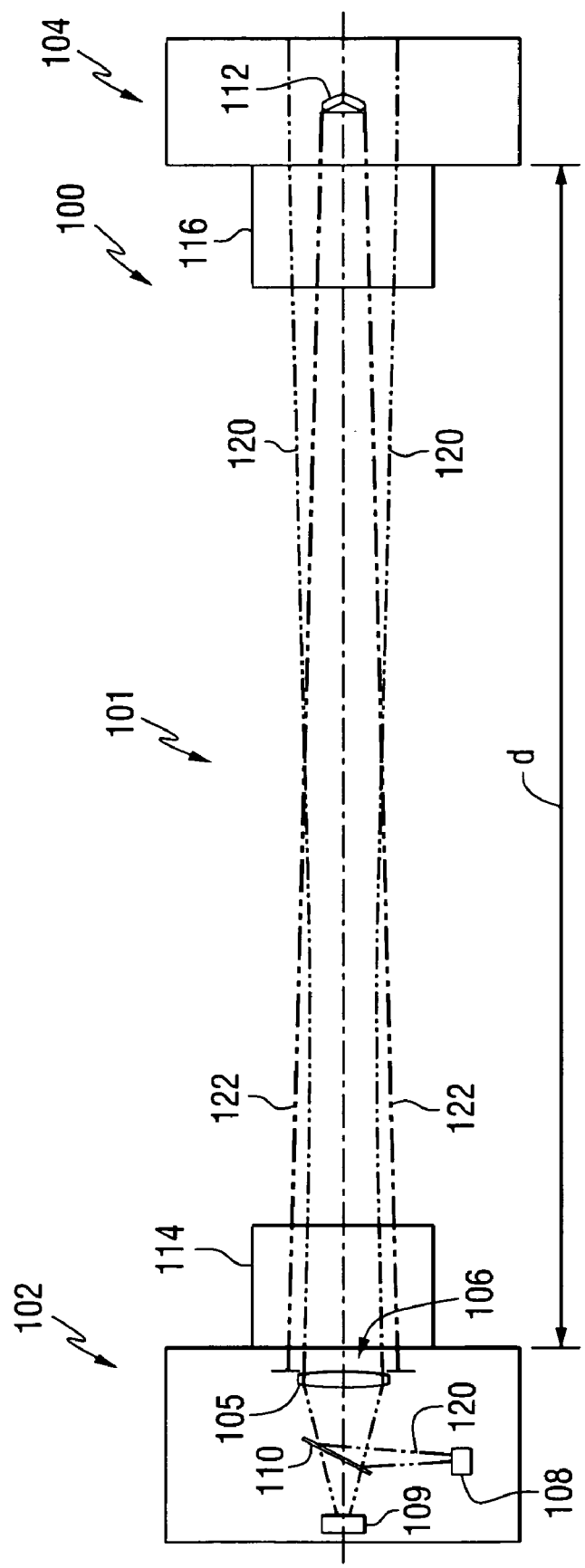
FIG. 1 shows a diagram of a prior art double pass opacity monitor, according to various embodiments.

Various embodiments of the present invention are directed to minimizing the negative bias in fluid measurement instruments by minimizing the effects of air lensing caused by purge fluid. Streams of purge fluid are often provided at the transceiver and/or reflector sides of opacity monitors and other fluid measurement instruments to direct contaminants, such as dirt or other particulate matter, away from optical devices. Air lensing occurs when the cooler fluid of a purge flow mixes with the hotter fluid of a stack in a regular manner. Because fluids of different temperatures have different indices of refraction, the interface between a cold purge flow and warm stack fluid can bend incident optical rays. Depending on the shape and characteristics of the interface, it may behave like a lens. Air lenses at the transceiver and reflector sides of opacity monitors can bend the forward and return beams 120, 122 as described below, resulting all or a portion of the negative bias that has been observed in fluid measurement instruments.

FIG. 2 shows an illustration of the transceiver unit 102 of double pass opacity monitor 100 illustrating an air lens 134. The transceiver unit 102 is shown mounted to a stack 103. A purge flow generator 130 may be connected to the purge nozzle 114 of the transceiver unit 102 via purge duct 132. The purge flow generator 130 may be any kind of mechanism suitable for generating a fluid flow including, for example, an air compressor, a source of compressed air, a squirrel cage blower, a pump, etc. The purge flow generator 130 may generate a purge flow, indicated by arrows 136, that travels to the nozzle 114 via the duct 132.

Figure 2A:
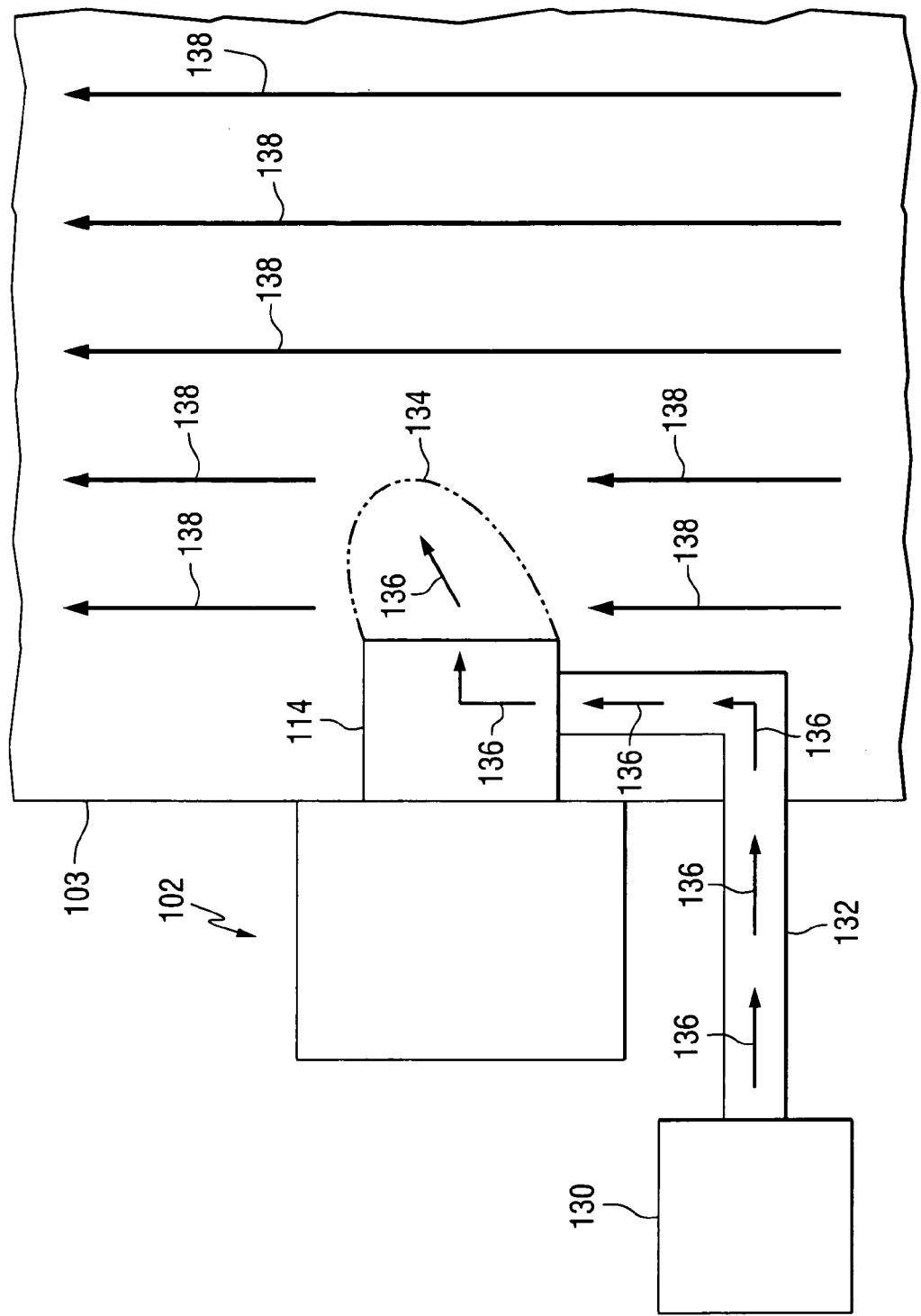
Figure 2B:
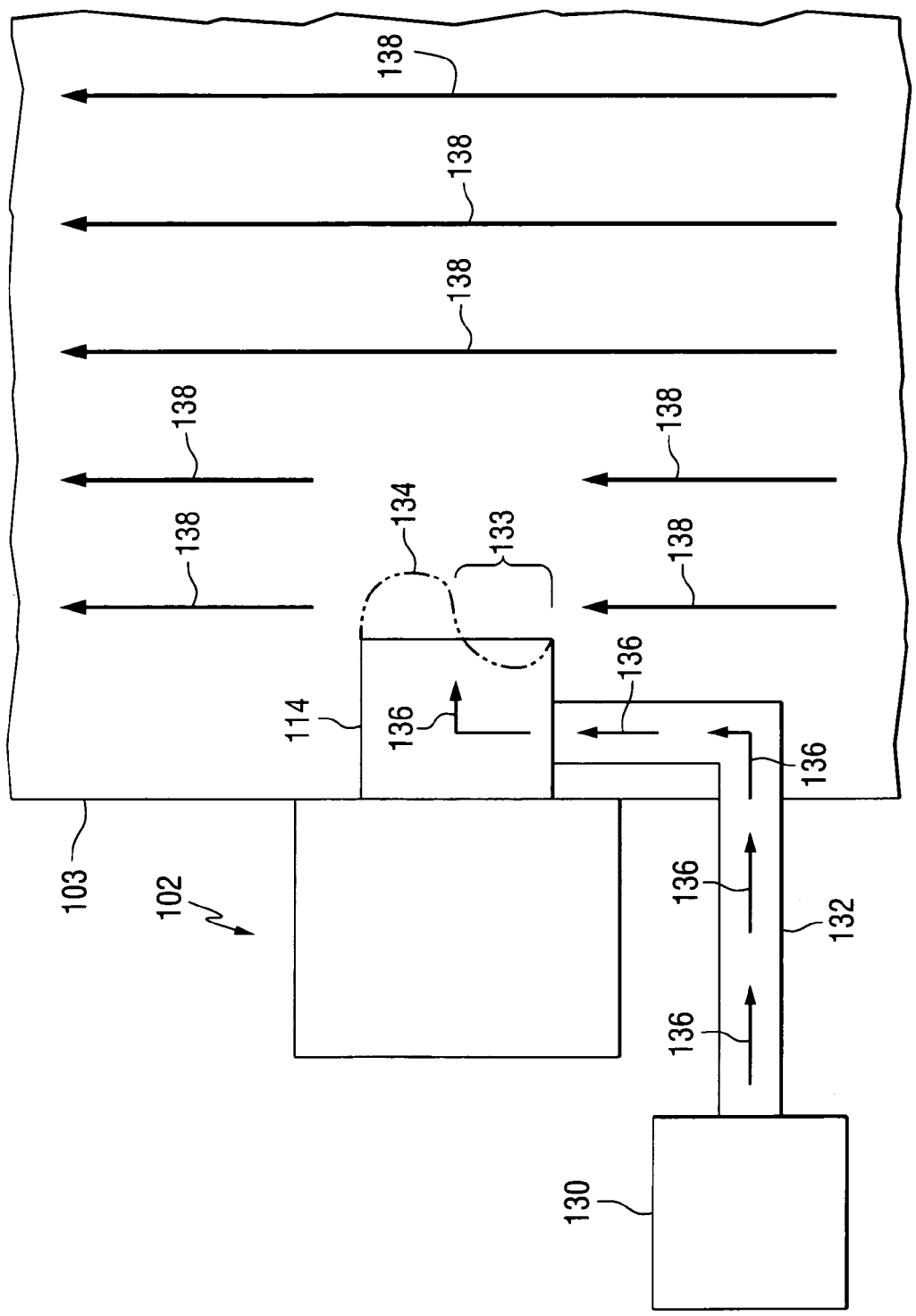

As the purge flow 136 traverses the duct 132 and nozzle 114, different portions of the flow 136 may acquire different properties. For example, the portions of the purge flow 136 that are near or in contact with the outer walls of the duct 132 and nozzle 114 may be heated by those walls, which are in contact with the hotter stack flow 138. In addition the portions of the purge flow 136 near or in contact with the outer walls of the duct 132 and nozzle 114 are slowed by friction between the walls and the purge flow 136. As a result, as the purge flow reaches the mouth of the nozzle 114, the central portions are colder and faster moving than the edge portions. Consequently, the temperature gradient between the purge flow 136 and the stack flow 138 forms a convex shape 134 which acts as an air lens. According to various embodiments, the motion of the stack flow 138 may have some effect on the shape of the air lens 134. For example, FIG. 2A shows a representation of the air lens 134 that is washed slightly upwards by the stack flow. Also, FIG. 2B shows a representation of the air lens 134 having a portion that is blown back into the nozzle 114 forming a concave section 133. It will be appreciated that although the air lens 134 is shown on the transceiver side of the opacity monitor 100, a similar air lens may be formed at the purge nozzle 116 of the reflector assembly 104.

Figure 3:
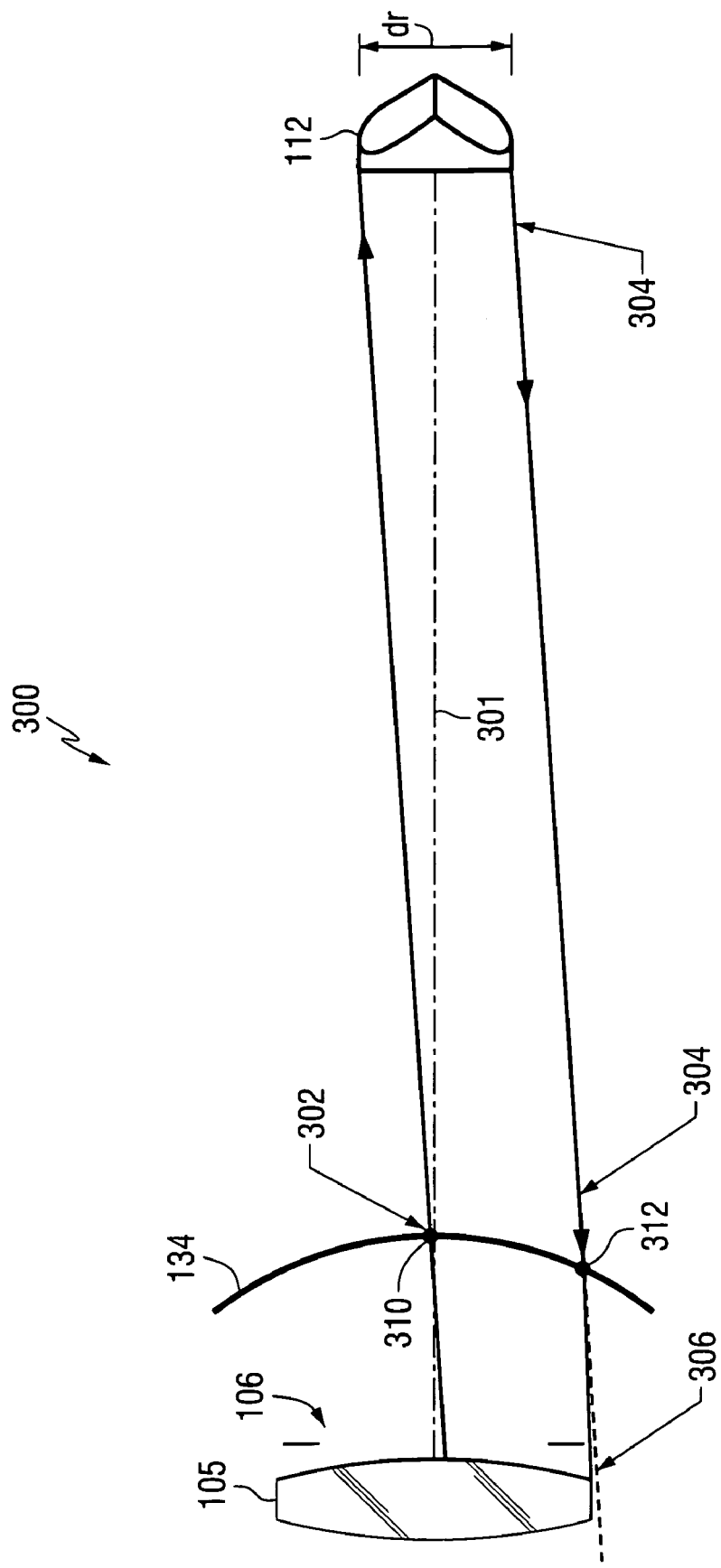
FIGS. 3 and 4 show illustrations of air lens effects, according to various embodiments.
Figure 4:
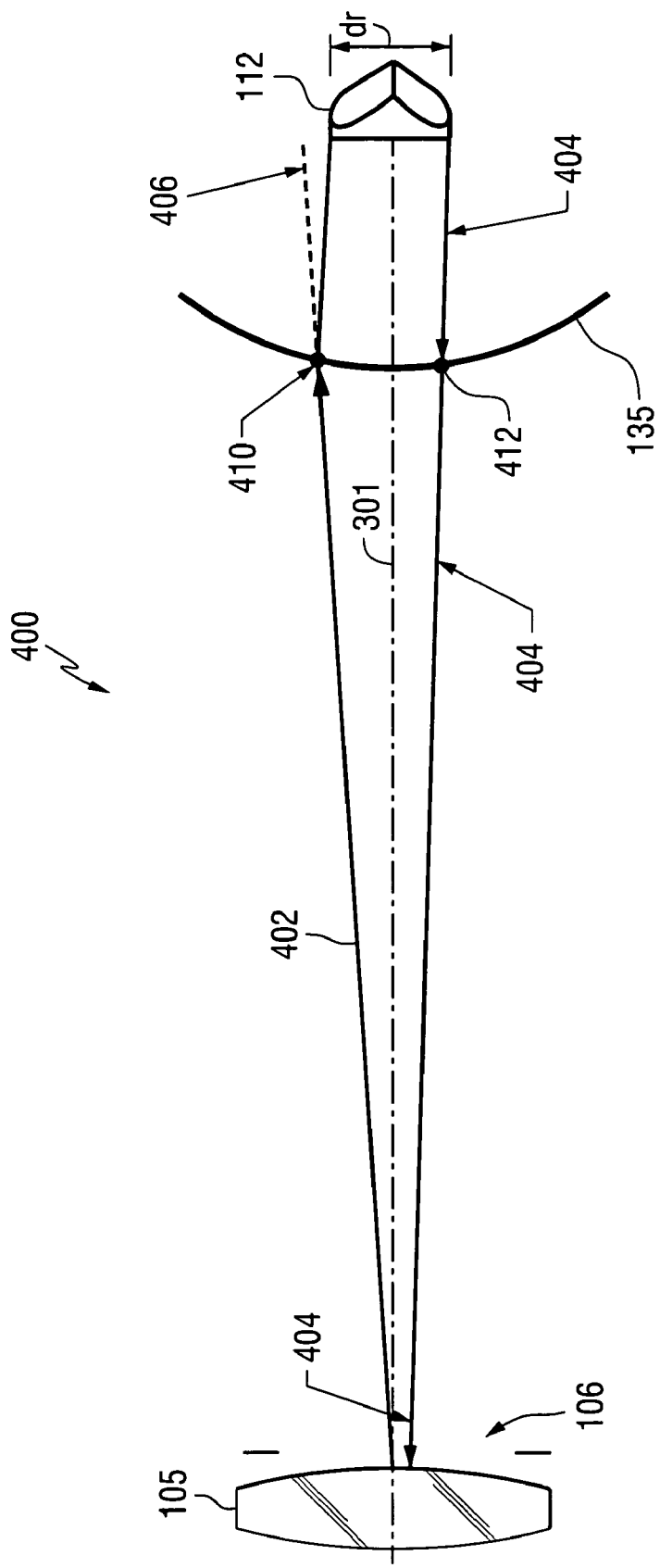

Air lenses at the transceiver side (FIG. 3) and the reflector side (FIG. 4) of the monitor 100 may bend the forward and return beams 120, 122 away from their expected paths, contributing to bias, as described below. The examples of FIGS. 3 and 4 are illustrated based on the focusing system of the monitor 100 shown in FIG. 1. It will be appreciated, however, that the effects outlined below may occur in other configurations as well. For example, some affected monitors utilize co-linear techniques, others may include additional optics, such as an imaging lens in front of the reflector 112, and others may omit various components, including, for example, the imaging lens 105.

FIG. 3 shows a diagram 300 illustrating the effects of a transceiver-side air lens. In the diagram 300, forward ray 302 is considered to be a portion of the forward beam 120 (not shown in FIG. 3) and return ray 304 is considered to be a portion of the return beam 122 (not shown in FIG. 3). As shown, the reflector 112 is sized to slightly over-fill the lens 105, as is common in double-pass opacity monitors. As shown, the forward ray 302 encounters the air lens 134 at a point 310 near the central axis 301 of the system. Because the air lens 134 may be relatively flat at point 310, minimal bending of the forward ray 302 may occur. After traversing the stack (not shown), the forward ray 302 encounters the corner cube reflector 112. When a ray, such as forward ray 302, encounters a corner cube, its direction is shifted by 180° and the ray is translated in space by a distance equal to the twice the distance between the point where the ray is incident on the corner cube and the central axis of the corner cube and in the opposite direction. For example, the forward ray 302, as illustrated, encounters the reflector 112 near its edge, so the distance from the point of incidence and the central axis 301 is ½ $d_r$, where $d_r$ is the diameter of the corner cube reflector 112. Accordingly, the ray 302 is translated by a distance equal to $d_r$. Although the diagram 300 represents this translation in two dimensions, it will appreciated that in practice, it occurs in three dimensions.

The reflected and translated ray is represented by return ray 304. The return ray 304 re-traverses the stack and is incident on the air lens 134 at a second point 312. Because of the translation effect of the corner cube, the second point 312 may not be near the first point 310. Also, because the point 312 is farther from the central axis 301, the air lens 134 may have a more severe curvature at point 312 than it has at point 310. Hence, the air lens 134 may bend the return ray 304 more severely than it did the forward ray 302. As a result, the return ray 304, which would have otherwise traveled along path 306 and missed the lens 105, is instead incident on the lens 105 and consequently sensed by the sensor 109 (not shown in FIG. 3).

When projected over the entire return beam 122, this effect of the transceiver-side air lens 134 causes a higher proportion of the return beam 122 to be incident on the sensor 109. This cancels out some of the effects of fluid opacity, causing negative bias in the readings of the opacity monitor 100. For example, opacity in the fluid attenuates some of the forward beam 120 and the return beam 122. The difference between the measured intensity of the return beam 122 and the intensity of the return beam 122 in an environment without opacity is interpreted as a measurement of opacity. When the air lens 134, however, causes the intensity of the return beam 122 to be artificially high, it reduces the measured difference and introduces negative bias to the monitor 100.

FIG. 4 shows a diagram 400 illustrating effects of an air lens 135 present at the reflector side of the opacity monitor 100. Ray 402 is considered to be a portion of the forward beam 120 and ray 404 is considered to be a portion of the return beam 122. As shown, the reflector 112 is over-filled by the forward beam 120, as is common. The ray 402 traverses the fluid and is incident on the air lens 135 at a point 410. The air lens 135 may bend the ray 402 toward the central axis 301 of the system, where it is incident on the reflector 112. The ray 402 is then reflected and spatially translated as described above. The reflected and translated ray is indicated as return ray 404. The return ray 404 is incident on the air lens 135 at point 412, where is it bent and directed back towards the lens 105. Absent the air lens 135, the forward ray 402 would have continued along the path 406 and missed the reflector 112, preventing it from being reflected and sensed by the sensor 109. When this effect is projected over the entirety of the beams 120, 122, it results in yet another increase in the observed intensity of the return beam 122, further exacerbating the negative bias of the monitor 100.

It will be appreciated that the effects described with respect to FIGS. 3 and 4 may be increased, reduced, or even reversed based on the shape of the air lens. For example, if stack conditions cause all or a portion of the air lens 134 to be concave, as shown by FIG. 2B, this may result in a positive opacity bias. Further, differences in the degree of curvature and the rate of change of curvature of the air lens 134 may increase or lessen the perceived negative bias. Also, reflector-side and transceiver-side air lenses 135, 134 may induce additional positive or negative biasing by affecting the focusing of the beams 120, 122 on the aperture 106 and reflector 112, for example.

Figure 5:
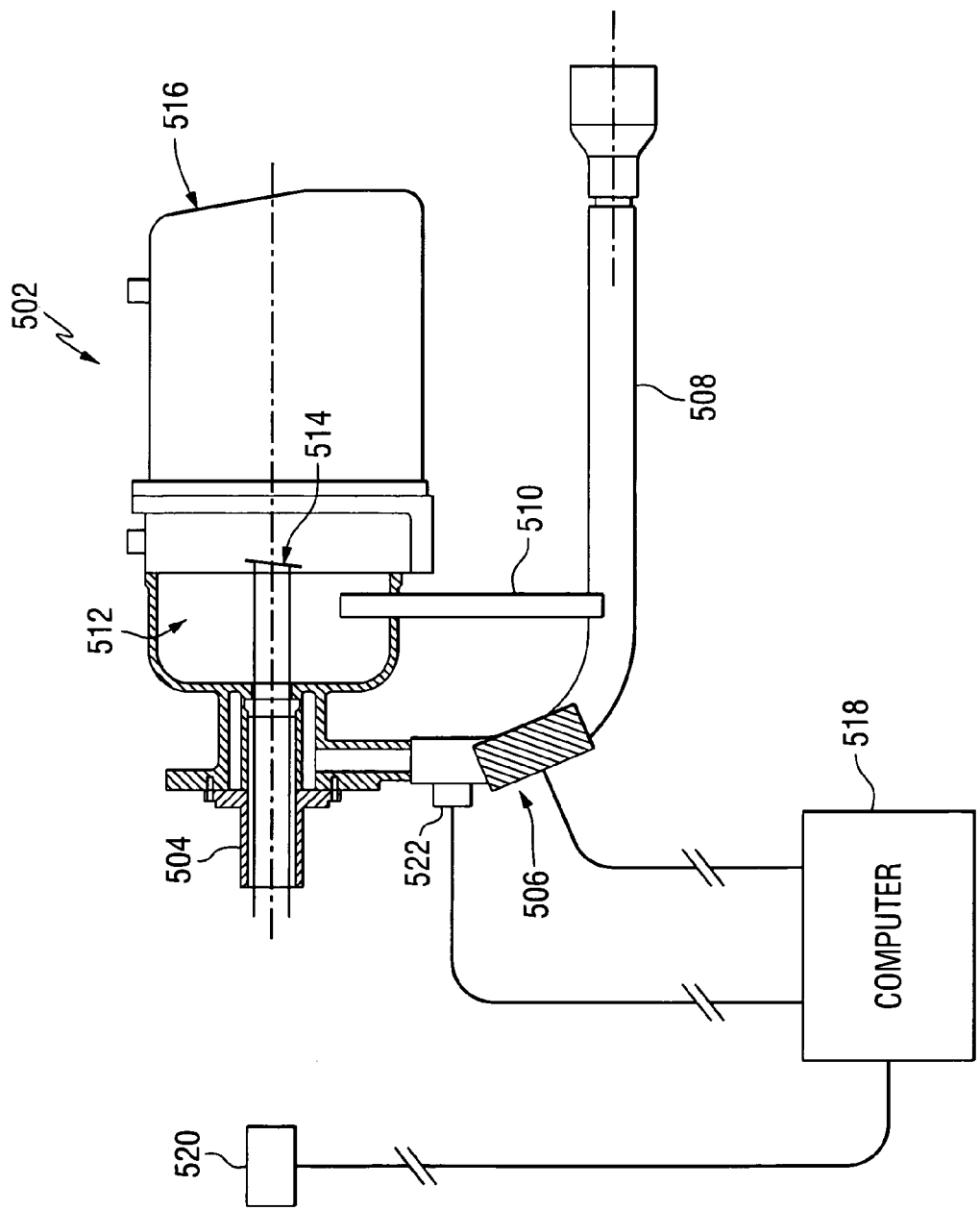
FIG. 5 shows a purge flow heater, according to various embodiments.

According to various embodiments, effects of the air lenses 134, 135 may be reduced by heating the purge flow to or near the temperature of the fluid to be measured (e.g., stack gas). In this way, the difference between the indices of refraction of the purge flow and the stack stream may be lessened, causing a corresponding lessening of the air lens effect. FIG. 5 shows a transceiver assembly 502, according to various embodiments, including functionality to heat a purge flow. The optical components of the transceiver assembly 502 may be enclosed in housing 516 and may interact with their outside environment via aperture 514. An optional plenum 512 may separate the housing 516 from a purge nozzle 504. Optical components enclosed by either the enclosure 516 or the plenum 512 may include, for example, one or more light sources, reflectors, imaging lenses, calibration-checking components, etc.

A purge duct 508 may route a purge flow from a purge flow generator (not shown) to the purge nozzle 504. The purge flow may initially be colder than the stack fluid. A purge flow heater 506 may be positioned around or in the purge duct 508 and may heat the purge flow relative to the stack fluid. According to various embodiments, a control system may be included to control the temperature of the purge flow. For example, the purge flow heater 506 may be in communication with a computer 518. The computer 518 may also be in communication with a sensor 520 positioned to sense a temperature of the stack fluid and/or a sensor 522 positioned to sense a temperature of the purge flow downstream of the heater 506. In this way, the computer 518 may control the operation of the purge flow heater 506 to achieve a desired temperature difference between the stack fluid and the purge flow and/or correlate the temperatures of the stack fluid and the purge flow fluid. It will be appreciated that the desired temperature difference between the stack fluid and the purge flow may be any suitable value including, for example, zero. In other various embodiments, a similar effect may be obtained by routing a portion of the purge duct 508 through the stack.

According to various embodiments, heating the purge flow may conduct an undesirable level of heat to the optical and other instrumentation of the transceiver assembly 502. Accordingly, a bypass duct 510 may allow cool fluid to enter and cool the enclosure. The bypass duct 510 may intersect a portion of the purge duct 508 that is upstream of the purge flow heater 506. In this way the bypass duct 510 may access purge fluid that has not yet been heated. This cool purge fluid may be deposited at a plenum 512 of the housing 516, where it may serve to cool the plenum 512 and housing 516. According to various embodiments, the shape of the plenum 512 may be designed to ensure as straight an interface as possible between the cool fluid of the plenum and the heated purge flow fluid in the purge nozzle 504. In this way, any air lensing effect between the nozzle fluid and the plenum fluid may be minimized.

Although the embodiments illustrated by FIG. 5 are described with respect to a transceiver assembly 502, it will be appreciated that similar devices and methods may be utilized with respect to a reflector assembly (not shown). Also, according to various embodiments, a single purge flow heater 506 may be used to heat the purge flows at the transceiver and reflector sides. Also, according to various embodiments, a single computer may control the operation of both a transceiver and a reflector purge flow heater 506.

Figure 6:
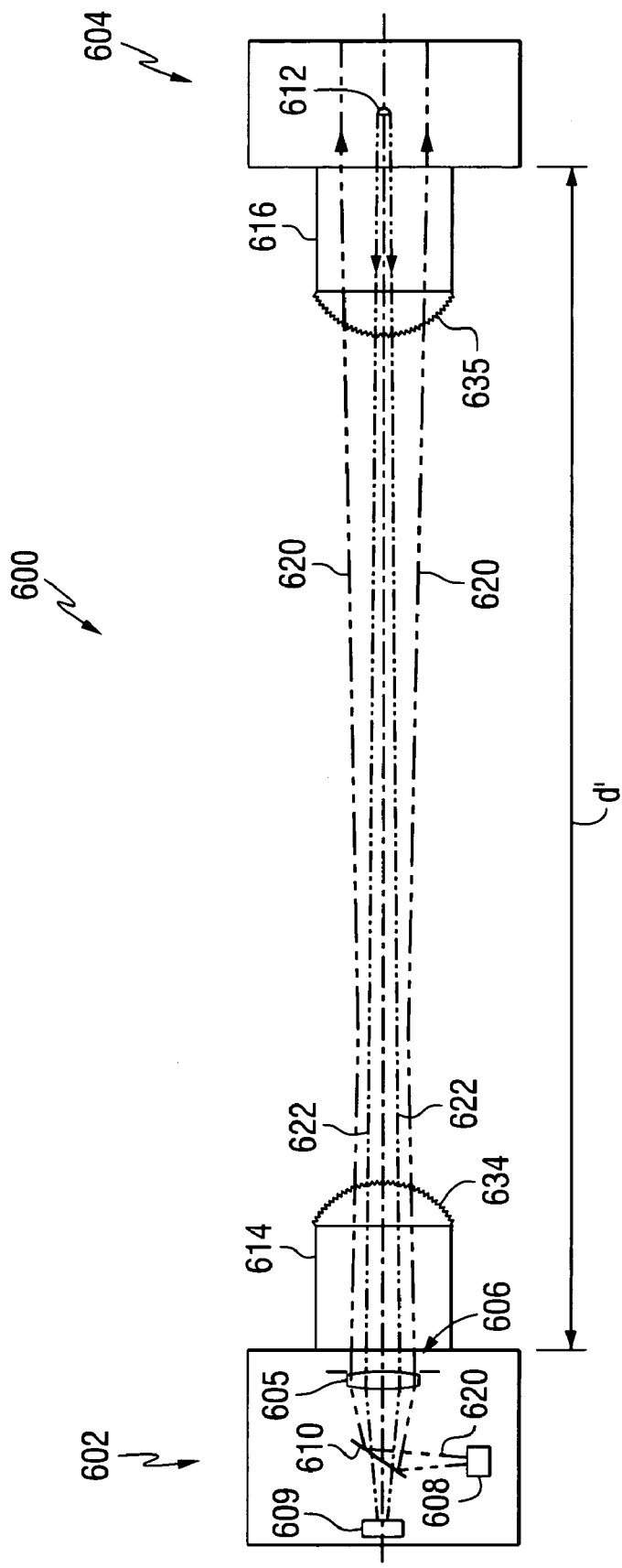
FIGS. 6-11 show a double-pass opacity monitor, according to various embodiments.
Figure 7:
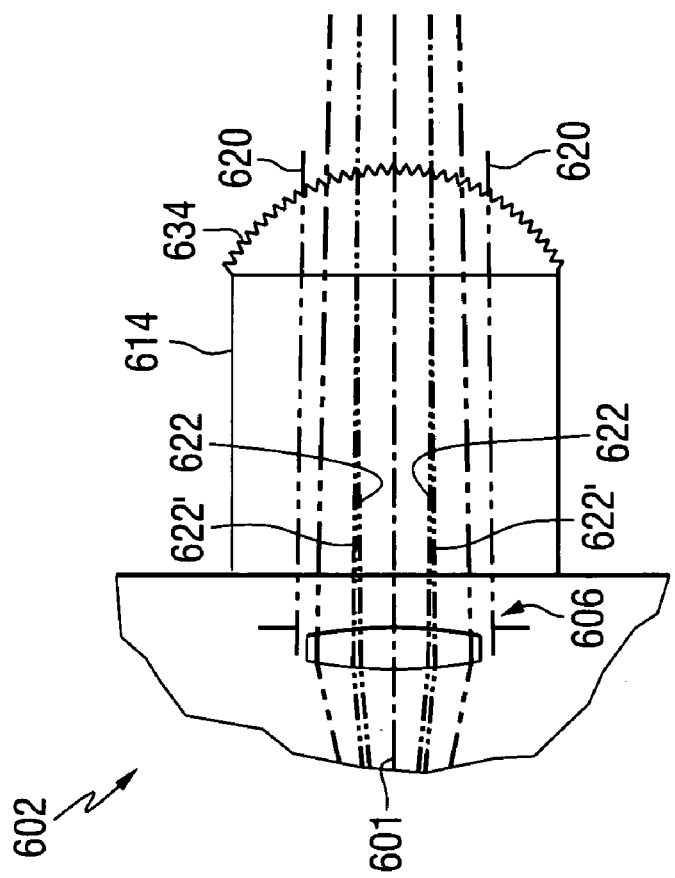

According to other various embodiments, the effects of air lensing may be minimized by reducing the size of the corner cube reflector relative to the receiver aperture and/or relative to the purge nozzle diameters. For example, FIG. 6 shows an opacity monitor 600 having a corner cube reflector 612 that is configured to under-fill the aperture 606. (It will be appreciated that the imaging lens 605 may be omitted.) FIG. 7 shows a diagram illustrating how this arrangement may reduce the effects of air lensing at the transceiver side of the device 600. The forward beam, shown by bounding rays 620 is emitted and directed toward the reflector 612 (not shown in FIG. 7). As the return beam, shown by bounding rays 622, is incident upon the air lens 624, it is converged toward the central axis 601. Because the aperture 606 is ordinarily under-filled, however, no additional optical energy reaches the sensor 609 as a result of the air lens. For example, had return beam 622 not encountered the air lens 634, it would have continued along the path shown by bounding rays 622'. The path 622' still intersects the aperture 606 and is still sensed by the sensor 609. Accordingly, there may not be any net gain of optical energy incident on the aperture 606.

Figure 8:
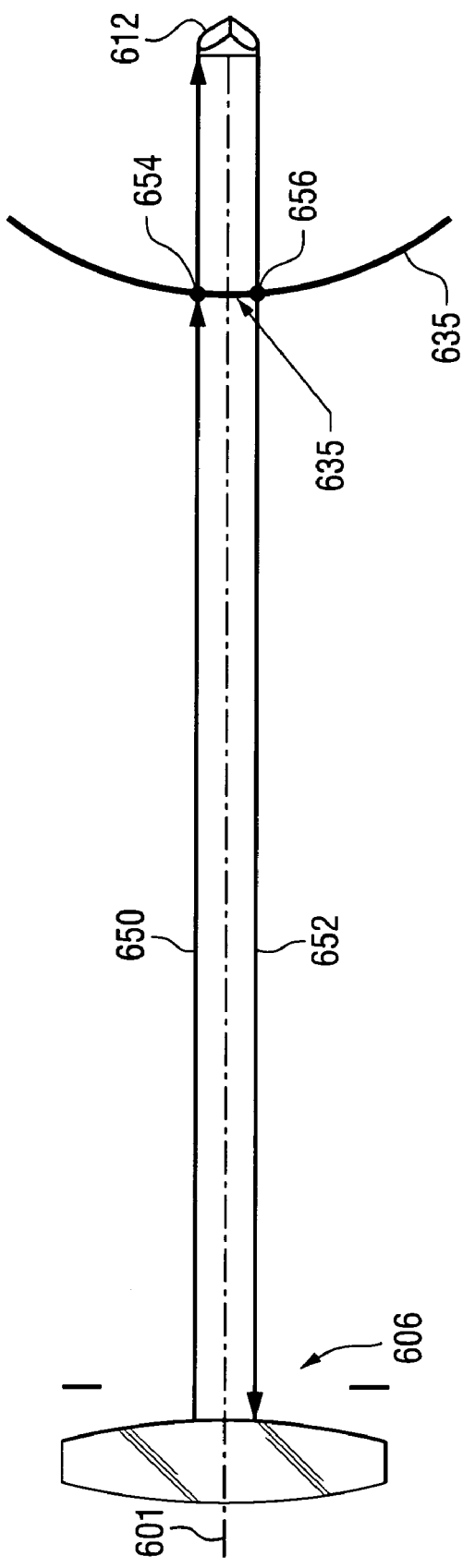

FIG. 8 shows a diagram illustrating how a smaller corner cube reflector 612 may reduce the effects of air lensing at the reflector side of the device 600 when the corner cube reflector 612 is mounted near the central axis 601. Forward ray 650 is considered to be a portion of the forward beam 620 and return ray 652 is considered to be a portion of the return beam 622. The forward beam 650 is emitted by the transceiver assembly 602, traverses the fluid and is incident on the air lens 635 at point 654. Because the point 654 is relatively close to the central axis 601, it may be relatively flat, resulting in relatively little bend to forward ray 650. Consequently, the portions of the forward beam 620 that are incident on the reflector 612 only as a result of the air lens 635 may be reduced, thus reducing intensity added to the return beam 622 by the air lens 635.

The forward ray 650 may be reflected and translated by the reflector 612. The result is marked as return ray 652. Because the diameter of the reflector 612 is small relative to the diameter of the air lens 635, the translation of the return ray 652 may also be small relative to the air lens 635. This may allow the return ray 652 to interface the air lens 635 at a point 656 that is near to point 654 and that may have a similar curvature to the point 654 (in FIG. 8, relatively little curvature). As a result, the path of the return ray 652 may be relatively parallel to that of the forward ray 650.

Figure 9:
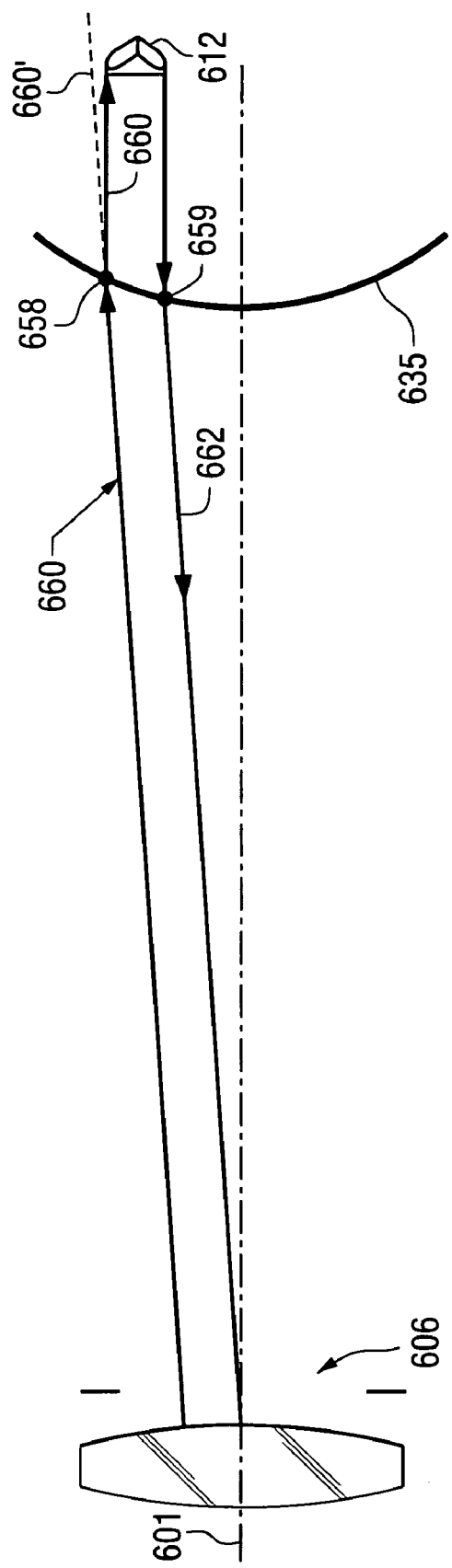
Figure 10:
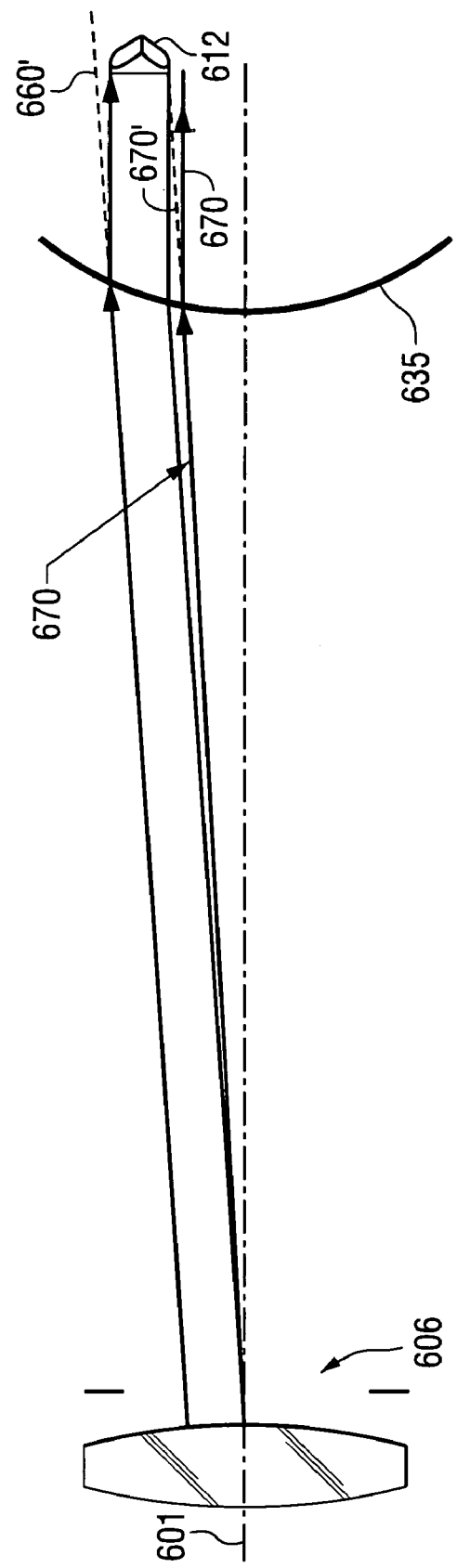

FIGS. 9 and 10 show diagrams illustrating how a smaller corner cube reflector 612 mounted off of the central axis 601 may reduce the effects of the air lens 635 at the reflector side of the monitor 600. As shown in FIG. 9, a forward ray 660, which is considered to be a portion of forward beam 620, is emitted by the transceiver assembly 602 and traverses the fluid to the air lens 635 where it is incident at point 658. Because the reflector 612 is mounted off of the central axis, the point 658 may be relatively far from the central axis 601 and therefore have a more severe curvature and bending effect. Accordingly, the forward ray 660, that would have otherwise continued along path 660' and missed the reflector 612, may be bent toward and intersect with the reflector 612 as shown. The reflected and translated return ray 662 may interface the air lens 635 at point 659. Again, because the diameter of the reflector 612 is small relative to the diameter of the air lens 635, point 659 may not be far from point 658 and may have a negligible difference in curvature. As a result, the return ray 662 may be incident on the aperture 606 along a path substantially parallel to that of forward ray 660.

As shown in FIG. 9, the forward ray 660 is reflected back to the aperture 606, even though, absent the air lens 635, it would have missed the reflector 612 and been lost. This may cause an increase in the intensity of the return beam 622, however, this increase may be offset by a corresponding portion of the forward beam 620 that the air lens 635 directs away from the reflector 612. Because the reflector 612 is small relative to the diameter of the air lens 635, most rays reaching the reflector 612 are incident on a portion of the air lens 635 having the same, or roughly similar, curvature. This means that the air lens 635 bends most of the rays incident on the reflector 612 by the same, or a similar amount. As a result, any portion of the forward beam 620 that reaches the reflector 612 only as a result of air lens bending (e.g., ray 660) is roughly canceled out by another portion of the forward beam 620 that misses the reflector 612 only as a result of the air lens 635. For example, FIG. 10 shows an example forward ray 670 that is also considered a part of the forward beam 620. The forward ray 670, but for the air lens 635, would have followed path 670' and been incident on the reflector 612. As a result of the air lens 635, however, the forward ray 670 is bent onto a path causing it to miss the reflector 612.

Figure 11:
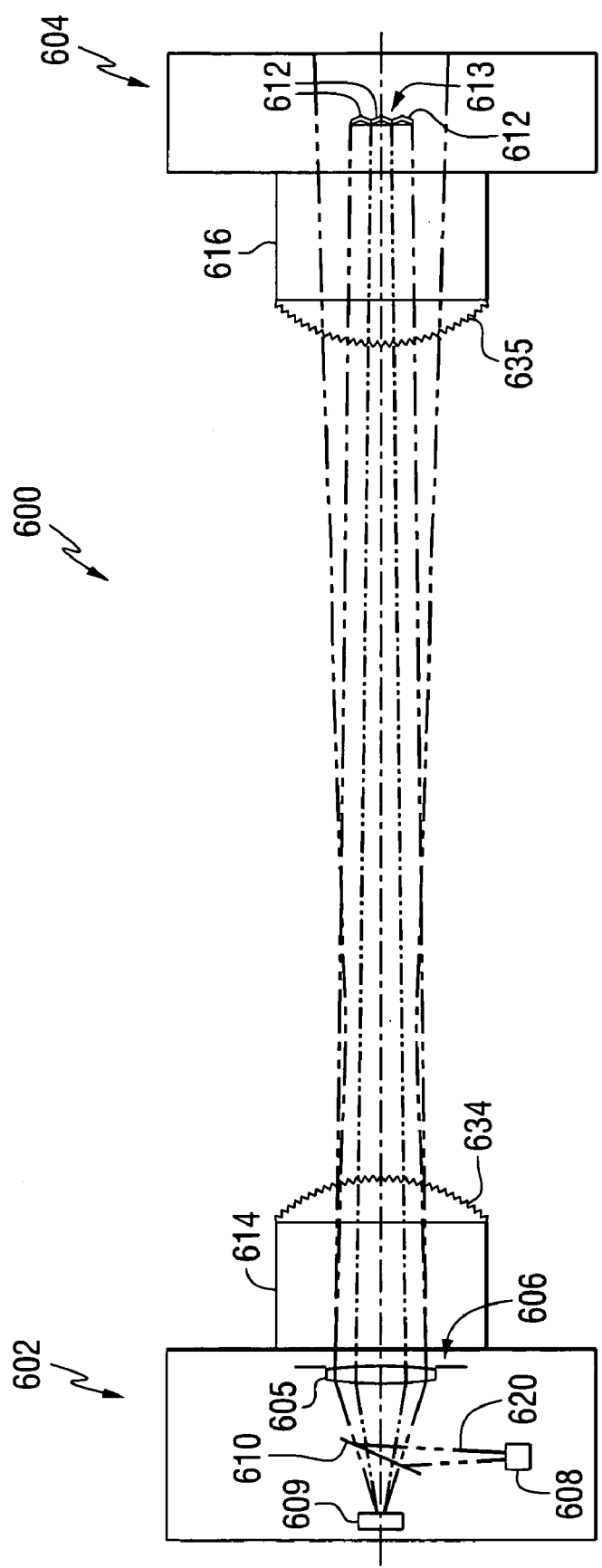

As described above, there are various disadvantages to selecting a reflector 612 that under-fills the aperture 606. For example, the intensity of the return beam 622 is lessened, reducing the signal-to-noise ratio of the monitor 600. Also, a smaller reflector 612 may be less likely to average out any non-uniformities of the beams 620, 622. These disadvantages may be overcome by using a plurality of retroreflectors 612, where each retroreflector is configured to under-fill the aperture 606 and/or be relatively small in diameter compared to the diameter of the air lenses 634, 635. For example, FIG. 11 shows an embodiment of the monitor 600 including an array 613 of reflectors 612. Each of the individual reflectors 612 of the array 613 may be configured to under-fill the aperture 606 and/or be relatively small in diameter compared to the diameter of the air lenses 634, 635. Because each of the reflectors 612 of the array 613 may under-fill the aperture 606, the effects of transceiver-side air lens 634 may be minimized as described above with respect to FIG. 7. Also, because each of the reflectors 612 of the array 613 may be relatively smaller than the diameter of the air lenses 634, and 635, the effects of the reflector-side air lens 635 may be minimized as described above with respect to FIGS. 8-10.

The degree to which the retroreflector or reflectors 612 under-fill the aperture 606 may be selected to minimize the air lensing affects. For example, although any degree of under-filling may reduce air lensing effects, according to various embodiments, the reflectors 612 may be selected to under-fill the aperture 609 by a factor of two (2) or greater. This means that the diameter of the aperture 609 may be two or more times greater than the diameter of the return beam 622 incident on the aperture. According to various embodiments, the reflectors 612 may be selected to under-fill the aperture 609 by a factor of two and one half (2.5) or greater. Also, the retroreflector or reflectors may be selected to under-fill the inner diameter of the purge nozzle 614 by any factor including, for example, a factor of two and one half (2.5) or greater. According to various embodiments, the retroreflector or reflectors 612 may be selected to under-fill the purge nozzle 614 by a factor of three (3).

Several methods are available for selecting a reflector 612 to under-fill the aperture 609 or purge nozzle 614 by a desired amount. For example, it could be assumed that the reflector 612 will ideally reflect each incoming ray by 180° and translate each incoming ray by twice the distance between the point of incidence and the center of the reflector. In this case, it may be assumed that the return beam 622 will diverge at the same rate as the forward beam 620. It may also be assumed the diameter of the return beam 622 at the aperture 606 is about twice the diameter of the reflector or reflectors 612. This is because the reflector 612 is positioned at the half-way point of the round trip of the forward and return beams 620, 622, and because when the reflectors 612 are over-filled, the initial diameter of the return beam 622 is equal to the diameter of the reflector 612. Accordingly, to achieve an under-fill factor of two (2), where the aperture 606 is about one (1) inch in diameter, the retroreflector or reflectors 612 may be chosen with a diameter of less than or equal to one fourth of one inch (0.25 inches). Also, to achieve an under-fill factor of two and one half (2.5), when the inside diameter of the purge nozzle 614 is one and one half (1.5) inches, the retroreflector may be selected with a diameter of less than or equal to three tenths (0.3) inches. According to various embodiments, the reflector selected may have the smallest reflector size that meets the desired under-fill factors for both the aperture 606 and purge nozzle 614.

In practice, corner cube reflectors are not ideal, and instead reflect incident rays at an angle of 180° plus or minus an imperfection factor, which may be represented as an angle, a. In various embodiments, it may be desirable to consider the non-idealities of corner cube reflectors to more accurately meet the desired under-fill factors. For example, in the set-up shown by FIG. 6, the maximum diameter of the return beam 622 is given by Equation (1) below:

$$\text{Max Diameter} = (2 * \text{Corner Cube Diameter}) + (2d' * \tan a) \quad (1)$$

Where, d' is equal to the distance between the reflector 612 and the aperture 606 (e.g., approximately the diameter of the stack) and a is an angle equal to the imperfection factor of the reflector 612. Considering Equation 1, a reflector 612 may be selected that under-fills the aperture 606 and/or the purge nozzle 614 by a desired amount. For example, to achieve an under-fill factor of 2.5, where the diameter of the aperture 606 is one (1) inch, it may be desirable to select a reflector or reflectors 612 that will deliver a return beam 622 with a diameter of about zero point four (0.4) inches. This may be accomplished by selecting a relatively large reflector with a small imperfection factor a. Where the distance d' is thirty (30) feet, the reflector may be selected with a diameter of zero point two (0.2) inches and a very small imperfection factor (e.g., six (6) arc seconds or less). It will be appreciated that reflectors with small imperfection factors may be quite costly. Accordingly, in various embodiments, it may be desirable to select a relatively small, inexpensive reflector with a higher imperfection factor a. For example, a reflector with a diameter of zero point one (0.1) inches and an imperfection factor of sixty (60) arc seconds may be chosen.

According to various embodiments, in addition to or instead of selecting a reflector 612 to under-fill the aperture 606 and/or the nozzle 614, the reflector 612 may be selected to have a diameter relatively smaller than the purge nozzle 616 and/or the purge nozzle 614. The air lenses 634 and 635 may be of approximately the same diameter as the inside diameter of the respective purge nozzles 614, and 616. Accordingly, selecting the reflector or reflectors 612 to be relatively smaller than one or both of the purge nozzles 614, 616, may have the effect of selecting a reflector 612 relatively smaller than the air lenses 634, 635. Any reflector 612 with a diameter less than the inside diameter of the purge nozzle 614 or 616, may reduce air lensing affects. According to various embodiments, however, the reflector or reflectors 612 may be selected to be smaller than the purge nozzle 616 (e.g., its inside diameter) by a factor of greater than or equal to five (5). For example, the reflector or reflectors 612 may be selected to be smaller than the purge nozzle 616 by a factor of at least six (6).

As described above with reference to FIGS. 2, 2A and 2B, the air lenses 634, 635 may change in shape and may even be partially or fully concave. It is believed that following the under-fill and size diameters disclosed can minimize the effects of air lenses, regardless of their orientation. For example, selecting a reflector 612 with a small diameter relative to the diameter of the air lens may minimize the amount of reflector translation relative to the face of the air lens whether the air lens is concave or convex. Also, under-filling the aperture 609 may leave an unused buffer around the edges of the aperture 609. Accordingly, the monitor may be able to tolerate a degree of return beam 622 divergence, as would be caused by a concave air lens.

Figure 12:
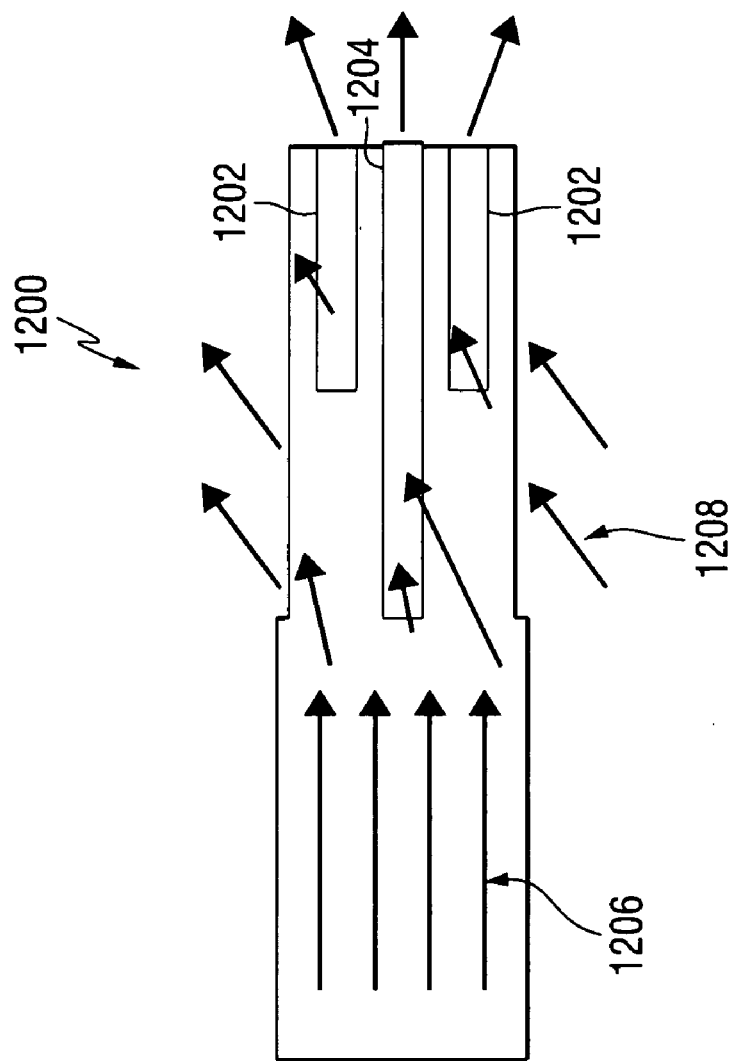
FIG. 12 shows a purge nozzle, according to various embodiments.

According to various embodiments, the effects of air lensing may be minimized by utilizing a purge nozzle or purge nozzles including openings for disrupting the purge flow before it exits the purge nozzle. For example, FIG. 12 shows an exemplary purge nozzle 1200 including openings 1202, 1204. The nozzle 1200 may be used at the transceiver side, the reflector side, or both. As shown, the openings 1202 and 1204 are slots, though it will be appreciated that any shaped opening may be used. Also, one or more of the openings, such as 1204 may be larger than the others. In use, the purge flow 1206 flows through the nozzle. Stack flow 1208 is incident on the nozzle 1200 and may enter the nozzle 1200 via slots 1202 and 1204. Also, portions of the purge flow 1206 may exit the nozzle 1200 via the slots 1202, 1204. In this way, the purge flow 1206 may be heated and mixed with the stack flow 1208 before reaching the end of the nozzle 1200. This may minimize the difference in temperature, and thus the difference in index of refraction, between the purge flow 1206 and the stack flow 1208 at the end of the nozzle 1200. In addition, it may disrupt the purge flow 1206, preventing a smooth air lens from forming.

According to various embodiments, some or all of the disclosed methods for minimizing the effects of air lensing may be used in conjunction with one another. For example, the monitor 600 may include reflectors 612 sized as described herein, as well a purge stream heater 506 and/or a purge nozzle 1200. It will be appreciated that when the various methods are used together, the desirable tolerances of each may be lessened. For example, if a purge stream heater 506 is used in conjunction with sized reflectors 612, then the purge stream heater 506 may not need to heat the purge stream to as high a temperature as might otherwise be desirable. Also, if sized reflectors 612 are used with a purge stream heater 506 or a nozzle 1200, they may, for example, support a smaller under-fill factor relative to the aperture 606 or the nozzle 114.

Other than the operating examples, or where otherwise indicated, all numbers expressing quantities of ingredients, processing conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained.

Notwithstanding that the numerical ranges and parameters setting forth the broad scope of the disclosure are approximations, the numerical values set forth in the specific examples are reported as precisely as possible. Any numerical values, however, inherently contain certain errors, such as, for example, equipment and/or operator error, necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of less than or equal to 10.

As used herein, a "computer" or "computer system" may be, for example and without limitation, either alone or in combination, a personal computer (PC), server-based computer, main frame, server, microcomputer, minicomputer, laptop, games console, personal data assistant (PDA), cellular phone, pager, state machine, relay array, processor, including wireless and/or wireline varieties thereof, and/or any other computerized device capable of configuration for processing data for standalone application and/or over a networked medium or media. Computers and computer systems disclosed herein may include operatively associated memory for storing certain software applications used in obtaining, processing, storing and/or communicating data. It can be appreciated that such memory can be internal, external, remote or local with respect to its operatively associated computer or computer system. Memory may also include any means for storing software or other instructions including, for example and without limitation, a hard disk, an optical disk, floppy disk, ROM (read only memory), RAM (random access memory), PROM (programmable ROM), EEPROM (extended erasable PROM), and/or other like computer-readable media.

While several embodiments of the invention have been described, it should be apparent that various modifications, alterations and adaptations to those embodiments may occur to persons skilled in the art with the attainment of some or all of the advantages of the present invention. It is therefore intended to cover all such modifications, alterations and adaptations without departing from the scope and spirit of the present invention as defined by the appended claims.

We claim:

1. An apparatus for measuring an optical property of a fluid, the apparatus comprising:

a light source for projecting a beam of optical energy through the fluid;

a reflector positioned opposite the fluid from the light source; and receiver optics defining a receiver aperture, wherein the reflector is selected to under-fill the receiver aperture by a factor of at least 2.5.

2. The apparatus of claim 1, further comprising a receiver purge nozzle positioned at least partially between the receiver optics and the fluid.

3. The apparatus of claim 2, further comprising a purge flow generator configured to emit a stream of purge fluid out of the receiver purge nozzle toward the fluid.

4. The apparatus of claim 3, further comprising a heater positioned to heat the stream of purge fluid.

5. The method of claim 3, wherein the purge flow generator comprises at least one item selected from the group consisting of a source of compressed air, an air compressor, a squirrel cage blower, and a pump.

6. The apparatus of claim 2, wherein the reflector is selected to under-fill the receiver purge nozzle by a factor of at least 3.

7. The apparatus of claim 2, wherein the receiver purge nozzle defines at least one mixing opening allowing the fluid to mix with the stream of purge fluid before the stream of purge fluid reaches the first opening.

8. The apparatus of claim 1, wherein the receiver optics further comprise a receiver lens positioned near the receiver aperture.

9. The apparatus of claim 1, wherein a diameter of the reflector is less than or equal to 20% of a diameter of the receiver aperture.

10. The apparatus of claim 1, further comprising a second reflector, wherein the second reflector is selected to under-fill the receiver aperture by a factor of at least 2.5.

11. The apparatus of claim 1, wherein the reflector is a corner cube reflector.

12. The apparatus of claim 1, wherein a diameter of the receiver aperture is 1 inch, wherein a distance between the receiver aperture and the reflector is 30 feet, and wherein the reflector has a diameter of 0.2 inches and an imperfection of 6 arc seconds.

13. The apparatus of claim 1, wherein a diameter of the receiver aperture is 1 inch, wherein a distance between the receiver aperture and the reflector is 30 feet, and wherein the reflector has a diameter of 0.1 inches and an imperfection of 60 arc seconds.

14. The apparatus of claim 1, further comprising a reflector purge nozzle positioned at least partially between the reflector and the fluid, wherein the reflector is also selected with a diameter less than a diameter of the reflector purge nozzle by a factor of at least 6.

* * * * *